US00PP21388P3

(12) United States Plant Patent
Meilland

(10) Patent No.: US PP21,388 P3
(45) Date of Patent: Oct. 19, 2010

(54) GRANDIFLORA ROSE PLANT NAMED 'MEIBIHARS'

(50) Latin Name: *Rosa hybrida*
Varietal Denomination: cv. Meibihars

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/379,445

(22) Filed: Feb. 23, 2009

(65) Prior Publication Data

US 2010/0218289 P1 Aug. 26, 2010

(51) Int. Cl.
*A01H 5/00* (2006.01)

(52) U.S. Cl. ..... Plt./132
(58) Field of Classification Search ..... Plt./131, Plt./132, 133, 134
See application file for complete search history.

*Primary Examiner*—June Hwu
(74) *Attorney, Agent, or Firm*—Buchanan Ingersoll & Rooney PC

(57) ABSTRACT

A new and distinct variety of Grandiflora rose plant is provided that abundantly forms on a nearly continuous basis attractive cream-colored blossoms that are margined with red. Blossoming commonly is initiated early in the season. A semi-erect low and substantially regular growth habit is displayed and the medium green foliage bears a glossy aspect. The blossoms emit a pleasant strong fragrance. The tolerance to diseases is normal with no particular susceptibility to diseases and pests having been found during observations to date. The plant is well suited for providing attractive ornamentation in parks and gardens.

2 Drawing Sheets

Figure 1:
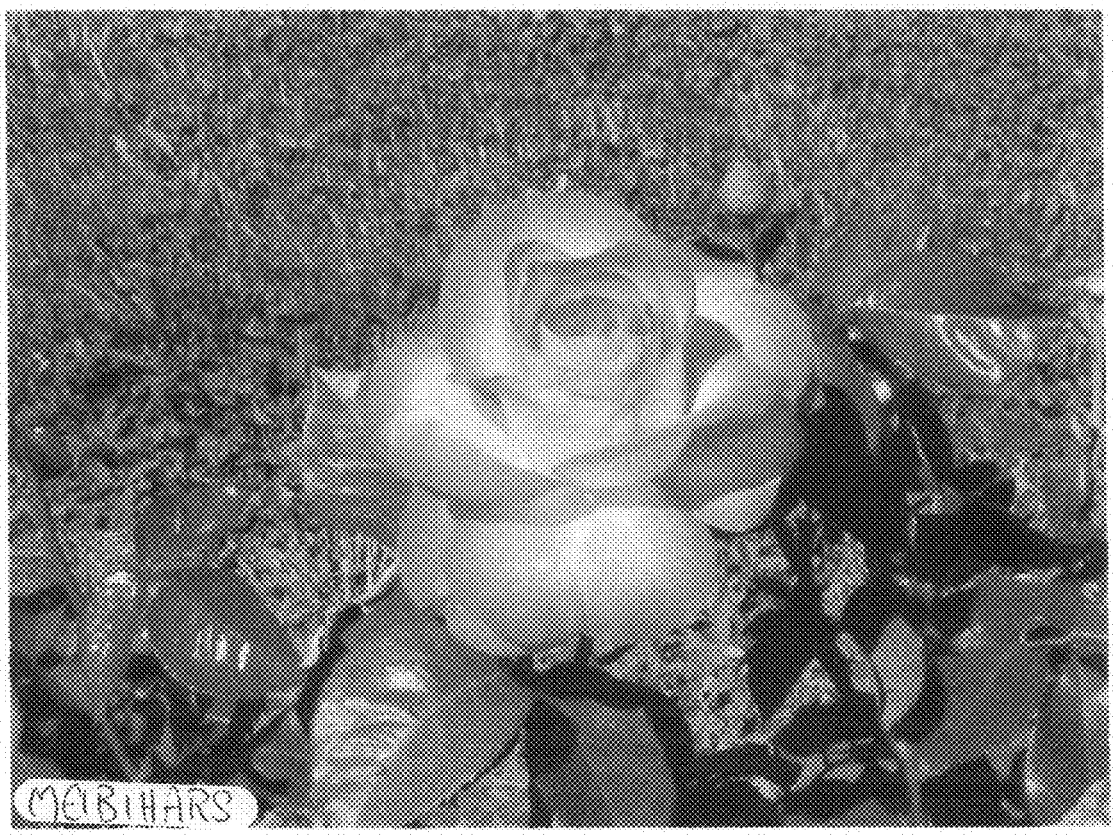

Botanical/commercial classification: *Rosa hybrida*/Grandiflora Rose Plant
Varietal denomination: cv. Meibihars

SUMMARY OF THE INVENTION

The new variety of *Rosa hybrida* Grandiflora rose plant was created by artificial pollination wherein two parents were crossed which previously had been studied in the hope that they would contribute the desired characteristics. The female parent (i.e., the seed parent) was the 'Meimagarmic' variety (U.S. Plant Pat. No. 5,067). The 'Meimagarmic' variety sometimes is marketed under the PRINCESSE DE MONACO Trademark. The male parent (i.e., the pollen parent) was the product of the cross of the 'Meihelvet' variety (U.S. Plant Pat. No. 3,095) and the 'Korsee' variety (non-patented in the United States). The 'Meihelvet' sometimes is known as the 'Sonia' and 'Sweet Promise'. The 'Korsee' variety sometimes is marketed under the UWE SEELER Trademark.

'Meimagarmic'×('Meihelvet'×'Korsee').

The seeds resulting from the above pollination were sown and small plants were obtained which were physically and biologically different from each other. Selective study resulted in the identification of a single plant of the new variety.

It was found that the new Grandiflora rose plant of the present invention:

(a) exhibits a semi-erect low and substantially regular growth habit,
(b) forms in abundance on a nearly continuous basis attractive cream-colored blossoms that are margined with red,
(c) displays attractive glossy medium green foliage,
(d) forms blossoms that emit a pleasant strong fragrance, and
(e) is particularly well suited for growing as attractive ornamentation in the landscape.

The new variety well meets the needs of the horticultural industry and can be grown to advantage as attractive ornamentation in parks and gardens. Blossoming commonly is initiated early in the season.

The new variety can be readily distinguished from its ancestors. For instance, the 'Meimagarmic' variety displays a more upright growth habit, and forms blossoms having a lesser number of petals which lack the strong fragrance of the new variety. The 'Meihelvet' variety blossoms have a lesser number of petals and are pink in coloration suffused with coral to yellow. The blossoms of the 'Korsee' variety display a dissimilar uniform salmon-orange coloration.

The new variety can be readily distinguished from the 'Meisponge' variety (U.S. Plant Pat. No. 12,802). More specifically, the blossoms of the 'Meisponge' variety tend to be somewhat smaller in size and to possess a more intense red margin coloration.

The new variety also can be readily distinguished from the 'Meikarady' variety (U.S. Plant Pat. application No. 12/453,591, filed May 15, 2009) upon an inspection of the blossom coloration. The blossoms of the 'Meikarady' variety possess a dissimilar red-purple margin with red coloration.

The new variety has been found to undergo asexual propagation at Le Luc, France by a number of routes, including budding, grafting, and the use of cuttings. Asexual propagation by the above-mentioned techniques in France has shown that the characteristics of the new variety are stable and are strictly transmissible by such asexual propagation from one generation to another.

The new variety has been named 'Meibihars'.

BRIEF DESCRIPTION OF THE PHOTOGRAPHS

The accompanying photographs show as nearly true as it is reasonably possible to make the same, in color illustrations of this character, typical specimens of the new variety. The rose plants of the new variety were approximately one year of age and were observed during October while budded on *Rosa laxa* understock and while growing outdoors at Le Cannet des Maures, Var, France.

Figure 2:
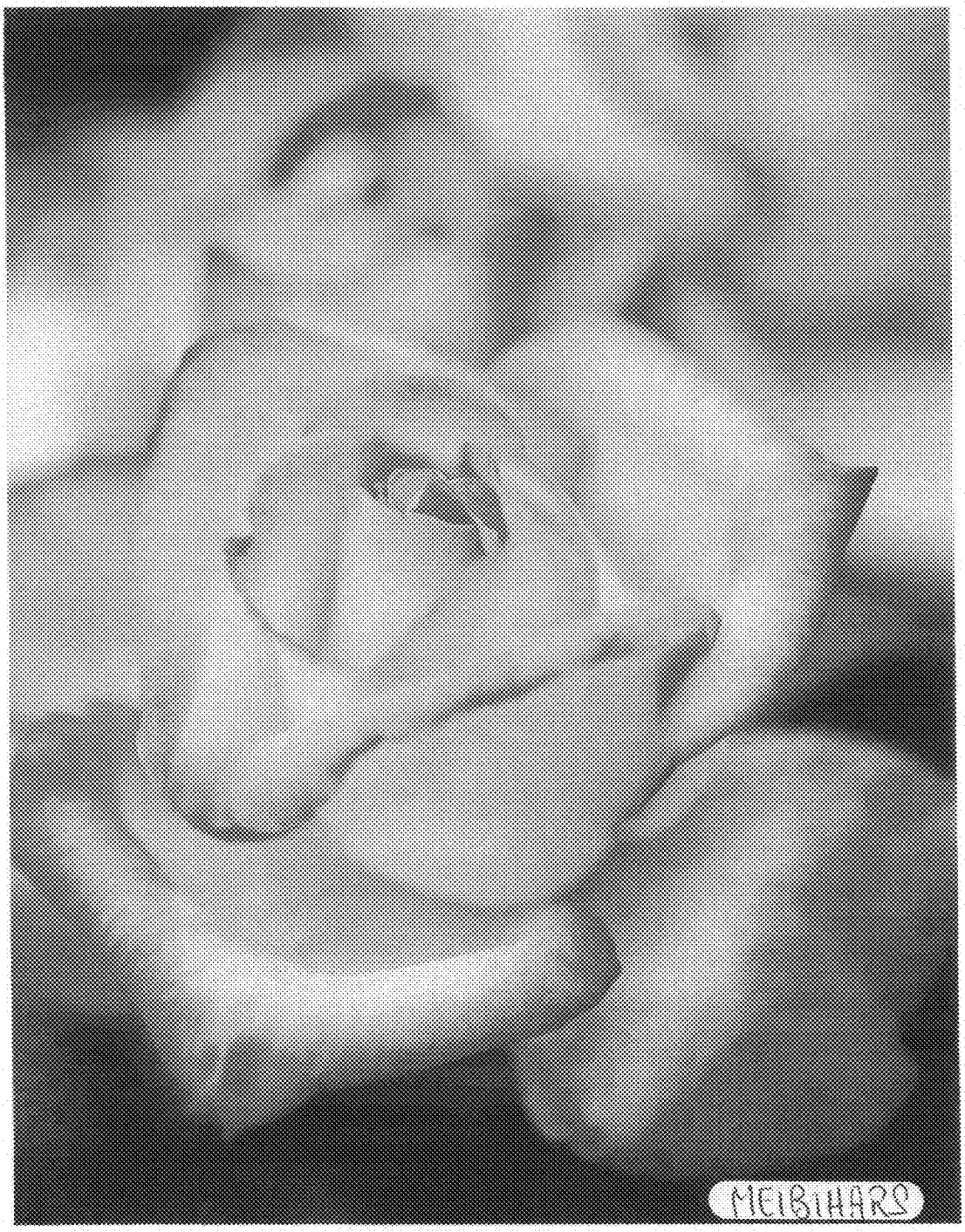

FIG. 1 — illustrates specimens of a typical blossom, bud, and foliage in various stages of development; and FIG. 2 — illustrates a close view of a typical specimen of a blossom of the new variety;

DETAILED DESCRIPTION

The chart used in the identification of the colors is that of the Royal Horticultural Society (R.H.S. Colour Chart). The description is based on the observation of one year-old plants during May while budded on *Rosa froebelii* understock and growing outdoors at Le Cannet des Maures, Var, France.

Class: Grandiflora.

Plant:

*Habit.*—Semi-erect.

Branches:

*Color.*—Young stems: near Green Group 143A. adult wood: near Green Group 141B.

*Thorns.*—On young stems: small prickles: configuration: upright on the upper surface and slightly concave on the under surface with a narrow base. quantity: approximately 5 on average on a stem length of 10 cm. length: approximately 0.3 cm. color: near Yellow-Green Group 152C. long prickles: configuration: upright on the upper surface and slightly concave on the under surface with a narrow and short base. quantity: approximately 6 on average on a stem length of 10 cm. length: approximately 0.6 cm on average. color: near Yellow-Green Group 153A. on adult stems: small prickles: configuration: upright and very longish pointed on the upper surface and slightly concave on the under surface with a narrow base. quantity: approximately 2 on average on a stem length of 18 cm. length: approximately 0.6 cm on average. color: near Greyed-Orange Group 166D. long prickles: configuration: upright and very longish pointed on the upper surface and slightly concave on the under surface with a narrow and short base. quantity: approximately 9 on average on a stem length of 18 cm. length: approximately 1 cm on average. color: near Greyed-Orange Group 164A.

Leaves:

*Stipules.*—General appearance: adnate, pectinate, and narrow. length: approximately 1.5 cm on average. width: approximately 0.5 cm on average. color (upper surface): near Green Group 141B. color (under surface): near Green Group 143A.

*Petioles.*—Length: approximately 2.9 cm on average for a terminal leaflet. upper surface: non-glandular, and near Green Group 141B in coloration. under surface: without prickles, and near Yellow-Green Group 144A in coloration.

*Rachis.*—Upper surface: near Green Group 143A in coloration. under surface: with some prickles, and near Yellow-Green Group 144B in coloration.

*Leaflets.*—Number: 3 and 5 (most often).

shape: generally elliptical with an acuminate tip and a rounded base. size: the terminal leaflets commonly are approximately 5.7 cm in length on average and approximately 3.8 cm in width on average. serration: small and single (as illustrated). texture: physically firm and thick. general appearance: dense and medium green with a glossy aspect. color (young foliage): upper surface: near Green Group 141A with reddish coloration of near Greyed-Purple Group 183A. under surface: near Yellow-Green Group 146B with reddish coloration of near Greyed-Purple Group 184A.. color (adult foliage): upper surface: near Green Group 139A. under surface: near Green Group 138A.

Inflorescence:

*Number of flowers.*—Commonly approximately 3 to 7 blossoms per stem on average.

*Peduncle.*—pubescent, approximately 6.5 cm in length on average, approximately 0.8 cm in diameter on average, and near Yellow-Green Group 144A in coloration.

*sepals.*—Configuration: long and narrow and somewhat upright at the base. upper surface: tomentose and near Green Group 137D in coloration. under surface: smooth and near Green Group 143A in coloration. size: near 3.2 cm in length on average, and near 0.9 cm in width at the widest point on average.

*Buds.*—Shape: globular. size: medium. length: approximately 3.5 cm on average. width: approximately 2.5 cm on average at the widest point. color (as the calyx breaks): upper surface: near White Group 155A suffused with Red Group 54B. under surface: near White Group 155B suffused with Red Group 56C.

*Flower.*—Sape: cup-shaped. diameter approximately 11 cm when open on average. color (in the course of opening): upper surface: near White Group 155A suffused with Red Group 55B, and with a spot of near Yellow Group 5B at the base. under surface: near White Group 155A suffused with Red Group 56D, and with a spot of near Green-Yellow Group 1C at the base. color (when fully open): upper surface: near White Group 155C suffused with Red Group 55C, and with a spot of near Yellow Group 5B at the base. under surface: near White Group 155B suffused with Red Group 56C, and with a spot of near Green-Yellow Group 1C at the base. fragrance: strong and pleasant. petal number: approximately 43 to 47 on average under normal growing conditions. petal shape: cuneiform base with a substantially rounded tip. petal texture: soft and flexible. petal length: commonly approximately 5.2 cm on average. petal width: commonly approximately 3.5 cm on average. petal arrangement: imbricated; and without petaloids. petal drop: good with the petals commonly detaching cleanly before drying. stamen number: approximately 90 on average. anthers: regularly arranged around the styles, approximately 0.4 cm in size on average, and near Yellow- Orange Group 17C in coloration. pollen: present and not currently available for inspection. filaments: approximately 0.8 cm in length on average and near Red Group 42B in coloration. pistils: approximately 65 on average. stigmas: approximately 0.2 cm in size on average and near Yellow-Orange Group 14B in coloration. styles: approximately 0.8 cm in length on average, and near Red Group 45D in coloration. receptacle: smooth, funnel- shaped in longitudinal section, approximately 1 cm in length on average, approximately 0.8 cm in width on average at the widest point, and near Green Group 143B in coloration. fruits/seeds: none observed during observations to date.

Development:

*Vegetation.*—Medium vigor.

*Blooming.*—Early, very abundant, and nearly continuous.

*Tolerance to diseases and pests.*—Normal, with no particular susceptibility to diseases and pests having been found during observations to date.

I claim:

1. A new and distinct Grandiflora rose plant characterized by the following characteristics:

(a) exhibits a semi-erect low and substantially regular growth habit, (b) forms in abundance on a nearly continuous basis attractive cream-colored blossoms that are margined with red, (c) displays attractive glossy medium green foliage, (d) forms blossoms that emit a pleasant strong fragrance, and, (e) is particularly well suited for growing as attractive ornamentation in the landscape;

substantially as herein shown and described.

* * * * *